US010201664B2

(12) United States Patent
Madsen et al.

(10) Patent No.: US 10,201,664 B2
(45) Date of Patent: Feb. 12, 2019

(54) DOSE CAPTURING CARTRIDGE MODULE FOR DRUG DELIVERY DEVICE

(71) Applicant: Novo Nordisk A/S, Bagsvaerd (DK)

(72) Inventors: John Oestergaard Madsen, Roedovre (DK); Jesper Peter Windum, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 409 days.

(21) Appl. No.: 14/767,506

(22) PCT Filed: Feb. 19, 2014

(86) PCT No.: PCT/EP2014/053219
§ 371 (c)(1),
(2) Date: Aug. 12, 2015

(87) PCT Pub. No.: WO2014/128155
PCT Pub. Date: Aug. 28, 2014

(65) Prior Publication Data
US 2016/0008552 A1    Jan. 14, 2016

Related U.S. Application Data

(60) Provisional application No. 61/767,820, filed on Feb. 22, 2013.

(30) Foreign Application Priority Data

Feb. 19, 2013   (EP) ...................................... 13155800

(51) Int. Cl.
*A61M 5/315*   (2006.01)

(52) U.S. Cl.
CPC ........ *A61M 5/31568* (2013.01); *A61M 5/315* (2013.01); *A61M 5/31565* (2013.01); *A61M 2205/52* (2013.01)

(58) Field of Classification Search
CPC .......... A61M 5/31568; A61M 5/31565; A61M 5/31583; A61M 5/3157
See application file for complete search history.

(56) References Cited

U.S. PATENT DOCUMENTS

| 4,807,248 A | 2/1989 | Pyatt et al. |
| 4,854,324 A | 8/1989 | Hirschman et al. |

(Continued)

FOREIGN PATENT DOCUMENTS

| CN | 201692426 U | 1/2011 |
| EP | 525525 A1 | 2/1993 |

(Continued)

*Primary Examiner* — Andrew M Gilbert
(74) *Attorney, Agent, or Firm* — Wesley Nicolas

(57) ABSTRACT

An electronic logging unit adapted to be housed in a drug-filled cartridge having an axially displaceable piston and an outer cavity formed between the piston and the cartridge proximal opening, the logging unit comprising a general axis, a first distal portion adapted to engage the cartridge piston, and a second proximal portion adapted to engage a rotating element having a rotational axis corresponding to the general axis. The unit is provided with sensor means adapted to detect the amount of relative rotation between the first and second portions, and storage means adapted to store data representing detected amounts of relative rotation.

13 Claims, 4 Drawing Sheets

(56) References Cited

U.S. PATENT DOCUMENTS

| | | |
|---|---|---|
| 4,891,476 A | 1/1990 | Nation et al. |
| 5,315,077 A | 5/1994 | Simon et al. |
| 5,480,387 A | 1/1996 | Gabriel et al. |
| 5,628,309 A * | 5/1997 | Brown .............. A61M 5/31525 128/DIG. 1 |
| 5,669,489 A | 9/1997 | von Ende |
| 5,739,775 A | 4/1998 | Brandestini |
| 5,847,335 A | 12/1998 | Sugahara et al. |
| 5,951,398 A | 9/1999 | Yamamoto et al. |
| 6,110,148 A * | 8/2000 | Brown ................ A61M 5/1782 222/23 |
| 6,277,099 B1 * | 8/2001 | Strowe .............. A61M 5/31553 604/186 |
| 6,585,698 B1 * | 7/2003 | Packman ................ A61M 5/24 604/207 |
| 7,008,399 B2 | 3/2006 | Larsen et al. |
| 7,138,806 B2 | 11/2006 | Gafner et al. |
| 7,195,616 B2 * | 3/2007 | Diller ................ A61M 5/31535 604/207 |
| 7,635,817 B2 | 12/2009 | Asada |
| 8,221,356 B2 | 7/2012 | Enggaard et al. |
| 9,750,886 B2 * | 9/2017 | Plambech ........... A61M 5/1452 |
| 2005/0115317 A1 | 6/2005 | Fouquet |
| 2006/0224123 A1 | 10/2006 | Freidli et al. |
| 2008/0033369 A1 | 2/2008 | Kohlbrenner et al. |
| 2008/0135090 A1 | 6/2008 | Corrales |
| 2008/0188813 A1 * | 8/2008 | Miller ................ A61M 5/14566 604/189 |
| 2008/0243088 A1 * | 10/2008 | Evans ................ A61M 5/31525 604/246 |
| 2009/0247951 A1 * | 10/2009 | Kohlbrenner ........... A61M 5/20 604/134 |
| 2009/0318865 A1 * | 12/2009 | Moller .............. A61M 5/31553 604/135 |
| 2010/0145656 A1 | 6/2010 | Koehler et al. |
| 2011/0009821 A1 * | 1/2011 | Jespersen ........... A61M 5/1452 604/135 |
| 2011/0270214 A1 * | 11/2011 | Jorgensen ......... A61M 5/31551 604/500 |
| 2011/0313349 A1 | 12/2011 | Krulevitch et al. |
| 2011/0313395 A1 | 12/2011 | Krulevitch et al. |
| 2012/0041363 A1 | 2/2012 | ielDan |
| 2012/0043131 A1 | 2/2012 | Christov et al. |
| 2013/0030383 A1 | 1/2013 | Keitel |
| 2013/0176020 A1 | 7/2013 | Chauvin et al. |
| 2014/0115910 A1 | 5/2014 | Hisamune et al. |
| 2014/0142511 A1 * | 5/2014 | Gilmore ............ A61M 5/31551 604/189 |
| 2014/0171879 A1 | 6/2014 | Butler et al. |
| 2014/0194825 A1 * | 7/2014 | Nielsen ................... A61M 5/24 604/189 |
| 2014/0243750 A1 * | 8/2014 | Larsen ................ A61M 5/1452 604/189 |
| 2014/0276583 A1 * | 9/2014 | Chen ................ A61M 5/31546 604/506 |
| 2015/0367077 A1 | 12/2015 | Plambech et al. |
| 2016/0015903 A1 * | 1/2016 | Madsen ................... A61M 5/24 604/211 |
| 2016/0175527 A1 | 6/2016 | McCullough |
| 2016/0287804 A1 | 10/2016 | Madsen et al. |
| 2016/0287807 A1 * | 10/2016 | Madsen ................... A61M 5/24 |
| 2016/0287808 A1 | 10/2016 | Madsen |

FOREIGN PATENT DOCUMENTS

| | | |
|---|---|---|
| EP | 1198811 A1 | 4/2002 |
| EP | 2060284 A1 | 5/2009 |
| EP | 1881859 B1 | 1/2011 |
| GB | 2456367 A | 7/2009 |
| WO | 96/019872 A1 | 6/1996 |
| WO | 9619872 A1 | 6/1996 |
| WO | 2005004955 A1 | 1/2005 |
| WO | 2006045525 A1 | 5/2006 |
| WO | 2008037801 A1 | 4/2008 |
| WO | 2008091838 A2 | 7/2008 |
| WO | 2008146282 A2 | 12/2008 |
| WO | 2009024562 A1 | 2/2009 |
| WO | 2010052275 A2 | 5/2010 |
| WO | 2010098927 A1 | 9/2010 |
| WO | 2010128493 A2 | 11/2010 |
| WO | 2011035877 A2 | 3/2011 |
| WO | 2011038703 A1 | 4/2011 |
| WO | 2011064299 A1 | 6/2011 |
| WO | 2012140097 A2 | 10/2012 |
| WO | 2013010889 A1 | 1/2013 |
| WO | 2013083715 A1 | 6/2013 |
| WO | 2013/098421 A1 | 7/2013 |
| WO | 2014/128156 A1 | 8/2014 |
| WO | 2014/128157 A1 | 8/2014 |

* cited by examiner

DOSE CAPTURING CARTRIDGE MODULE FOR DRUG DELIVERY DEVICE

CROSS-REFERENCE TO RELATED APPLICATIONS

This application is a 35 U.S.C. § 371 National Stage application of International Application PCT/EP2014/053219 (published as WO 2014/128155), filed Feb. 19, 2014, which claims priority to European Patent Application 13155800.9, filed Feb. 19, 2013; this application claims priority under 35 U.S.C. § 119 to U.S. Provisional Application 61/767,820; filed Feb. 22, 2013.

The present invention relates to a module, device and method for capturing drug delivery dose data. Especially, the invention addresses the issue of providing an electronic data capturing system for and in a drug delivery device.

BACKGROUND OF THE INVENTION

In the disclosure of the present invention reference is mostly made to the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems. Thus, a number of injection devices with a dose monitoring/acquisition feature has been provided, see e.g. in US 2009/0318865, WO 2010/052275 and U.S. Pat. No. 7,008,399. However, most devices of today are without it.

Correspondingly, data acquisition/monitoring functionality have been proposed to be provided in a separate device to be put on or in the injection device, i.e. some kind of accessory e.g. an add-on module to the injection device.

For example, WO 2010/098927 discloses a medical module which is configured to be attached to a drug delivery pen, the module being adapted to detect and store selected and ejected dosages as well as other data. Further arrangements adapted to capture dose data are known from WO 2010/128493, EP 2 060 284, WO 2010/052275 and WO 2009/024562.

Having regard to the above, it is an object of the present invention to provide a drug delivery device as well as components therefore which cost-effectively and reliably allows detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention an electronic logging unit (or module) adapted to be housed in a drug-filled cartridge outer cavity is provided, the cartridge comprising a tubular main portion with a proximal opening, a distal outlet portion, and an axially displaceable piston arranged in the tubular main portion at a distance from the proximal opening, the outer cavity being formed between the piston and the proximal opening. The logging unit comprises a general axis, a first distal portion adapted to engage the cartridge piston, a second proximal portion adapted to engage a rotating element having a rotational axis corresponding to the general axis, sensor means adapted to detect the amount of relative rotation between the first and second portions, and storage means adapted to store data representing detected amounts of relative rotation. By this arrangement a logging unit can be provided in an otherwise un-modified drug delivery device comprising a piston rod rotating during dose delivery, the rotation being transferred to the proximal portion of the logging unit. This said, it may be necessary to use a cartridge with a more distally arranged piston in order to make room for the logging unit.

The log will typically be in the form of a number of events comprising data representing a dose amount in combination with a time value. The stored data may be in the form or rotation data only, this allowing the receiving unit, e.g. a smartphone or PC, to calculate the actual drug dose amounts based on supplied information in respect of the type of drug, type of cartridge, and type of device. Alternatively, the logging unit may be pre-programmed to work only with a given drug in a given device. Correspondingly, the stored time data may be a relative time indication which is then translated into absolute time in the receiving device.

The logging unit may be provided as an "ad-on" allowing a conventional durable, i.e. reusable, drug delivery device to be provided with a logging functionality when needed. For example, when initiating a given patient on an insulin regimen the prescribing doctor may provide the patient with a drug delivery device in which a logging unit has been inserted, this allowing the doctor to check to which degree the patient has been in compliance with the regiment when the device is returned to the doctor after use. Indeed, the same logging unit could be used on a regular basis by any patient for which the logging capability and user interface are desirable. Alternatively the logging unit could be provided in a disposable, pre-filled device although this concept may only be cost-effective for limited use, e.g. when initializing a patient on an insulin regimen. For ease of use the logging unit may be provided with wireless communication, e.g. based on energy-saving passive NFC, this allowing data to be uploaded to any NFC-enabled device such as a smartphone. If the logging unit is intended to be removed from the cartridge after use also a galvanic contact could be used.

In an exemplary embodiment the logging unit comprises a first portion adapted to engage the cartridge, e.g. the piston and/or the cartridge wall, the engagement preventing rotational movement between the first portion and the cartridge during expelling of a dose of drug, and a second portion adapted to engage the piston rod, the engagement preventing rotational movement between the second portion and the piston rod during expelling of a dose of drug, wherein the first and second portions are adapted to be both moved axially corresponding to axial movement of the piston and piston rod. The logging unit may be designed to be positioned between the piston and the piston rod such that the piston rod during expelling of a dose exerts a distally directed force on the logging unit, the force being transferred to the piston by the logging unit. The rotation preventing engagement may be based on form and/or friction. The applied force could also be used to activate a contact to thereby turn on the unit.

The first portion may comprise electronic circuitry, and a first rotary sensor part, whereas the second portion may comprise a second rotary sensor part, such that the first and second parts of the rotary sensor rotate relative to each other during expelling of a dose of drug. The circuitry will typically comprise a processor in the form of a microprocessor, microcontroller or CPU which may be of a general purpose design or be specifically designed for the actual device.

The rotary sensor may be based on any desirable technology allowing relative rotation between the two components to be detected, however, the technology should fulfil given requirements in being compact, reliable, cost-effective and energy-effective. In an exemplary embodiment the first rotary sensor part comprises a pattern of a plurality of individual electrically conducting sensor areas connected to the electronic circuitry, and the second rotary sensor part comprises at least one contact structure (e.g. two contact arms electrically connected to each other) adapted to engage and connect different sensor areas as the first and second part of the rotary sensor rotate relative to each, the connections being indicative of a rotational position between the first and second portions.

Adapted for the specific purpose of being arranged in a given drug cartridge the logging unit may have an effective diameter of less than 30 mm, less than 20 mm, less than 15 mm, or less than 10 mm.

In a further aspect of the invention an electronic logging unit as described above is provided in combination with a cartridge comprising a tubular main portion with a proximal opening, a distal outlet portion, and an axially displaceable piston arranged in the tubular main portion at a distance from the proximal opening, an outer cavity being formed between the piston and the proximal opening, wherein the logging unit is housed in the cartridge outer cavity.

In a yet further aspect of the invention an electronic logging unit as described above is provided in combination with a drug delivery device comprising a drug-filled cartridge and drug expelling means. The drug-filled cartridge comprises a generally tubular main portion with a proximal opening, a distal outlet portion, and an axially displaceable piston arranged in the tubular main portion at a distance from the proximal opening, an outer cavity being formed between the piston and the proximal opening. The drug expelling means comprising an axially displaceable piston rod adapted to move the piston of a cartridge in a distal direction to thereby expel drug from the cartridge, the piston rod rotating relative to the cartridge during axial movement. The electronic logging unit is initially arranged at least partly in the cartridge outer cavity and being configured to be moved fully there into, the sensor means being adapted to detect the amount of relative rotation between the piston rod and the cartridge during expelling of a dose of drug, the amount of relative rotation corresponding to the dose amount of drug expelled, the storage means adapted to store data representing expelled dose amounts.

In an exemplary embodiment engagement of the first portion and the cartridge prevents rotational movement there between during expelling of a dose of drug, and engagement of the second portion and the piston rod prevents rotational movement there between during expelling of a dose of drug, the first and second portion being adapted to be moved axially corresponding to axial movement of the piston and piston rod.

During expelling of a dose of drug the distally directed force on the logging unit may be transferred to the piston by the logging unit.

In a yet further aspect of the invention a method for providing a drug delivery device adapted to create a log for expelled amounts of a drug is provided, the method comprising the steps of providing (i) a drug-filled cartridge comprising a generally tubular main portion with a proximal opening, a distal outlet portion, and an axially displaceable piston arranged in the tubular main portion at a distance from the proximal opening, an outer cavity being formed between the piston and the proximal opening, (ii) a drug delivery device adapted to receive the drug-filled cartridge, comprising drug expelling means comprising dose setting means allowing a user to set a dose of drug to be expelled from a received drug-filled cartridge, and an axially displaceable piston rod adapted to move the piston of a received drug-filled cartridge in a distal direction to thereby expel drug from the cartridge, the piston rod rotating relative to the cartridge during axial movement, and (iii) an electronic logging unit adapted to be arranged initially at least partly in the cartridge outer cavity and being configured to be moved fully their into, the logging unit comprising sensor means adapted to detect the amount of relative rotation between the piston rod and the cartridge during expelling of a dose of drug, the amount of relative rotation corresponding to the dose amount of drug expelled, and storage means adapted to store data representing expelled dose amounts. The method comprises the further step of (iv) arranging the drug-filled cartridge and the logging unit in the drug delivery device, the logging unit being arranged at least partly in the cartridge outer cavity. The provided logging unit may comprise a first portion adapted to engage the piston, the engagement preventing rotational movement between the first portion and the piston during expelling of a dose of drug, and a second portion adapted to engage the piston rod, the engagement preventing rotational movement between the second portion and the piston rod during expelling of a dose of drug, wherein the first and second portions are adapted to be moved axially corresponding to the axial movement of the piston and piston rod.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
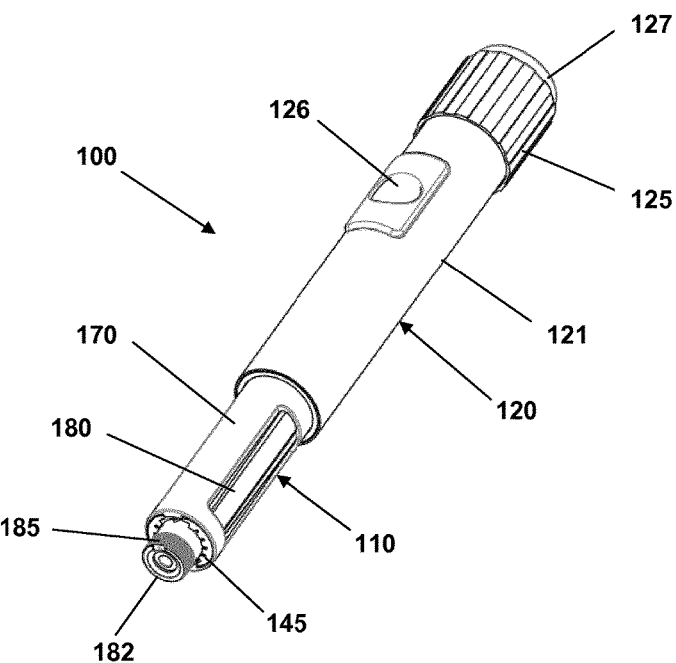
FIGS. 1 and 2 show a front-loaded drug delivery device with respectively without a drug cartridge mounted.

Referring to FIG. 1 a pen-formed drug delivery device 100 will be described. The device represents a "generic" drug delivery device providing an example of a device in combination with which embodiments of the present invention is intended to be used, such a device comprising a piston rod which rotates during expelling of a dose of drug.

Figure 2:
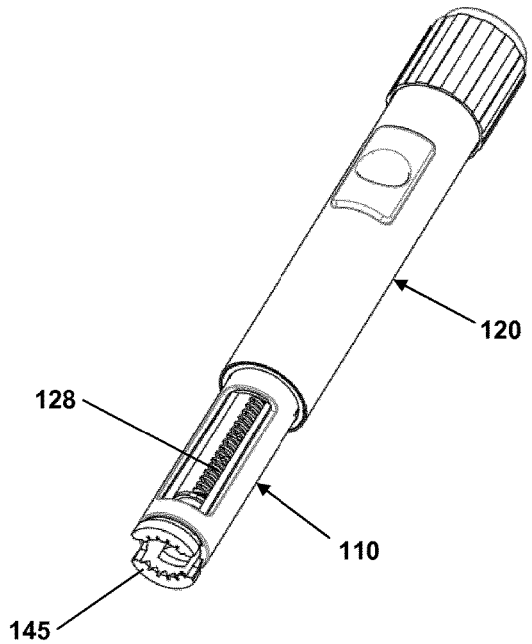

More specifically, the pen device comprises a cap part (not shown) and a main part having a proximal body or drive assembly portion with a housing 120 in which a drug expelling mechanism is arranged or integrated, and a distal cartridge holder portion in which a drug-filled transparent cartridge 180 with a distal needle-penetrable septum 187 can be arranged and retained in place by a cartridge holder 110 attached to the proximal portion, the cartridge holder having openings allowing a portion of the cartridge to be inspected. The cartridge may for example contain an insulin, GLP-1 or growth hormone formulation. The device is designed to be loaded by the user with a new cartridge through a distal receiving opening in the cartridge holder, the cartridge being provided with a piston driven by a piston rod 128 forming part of the expelling mechanism. A proximal-most rotatable dose ring member 125 serves to manually set a desired dose of drug shown in display window 126 and which can then be expelled when the release button 127 is actuated. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 182 having, in the shown example, an external thread 185 adapted to engage an inner thread of a corresponding hub of a needle assembly. In alternative embodiments the thread may be combined with or replaced by other connection means, e.g. a bayonet coupling. The shown exemplary hub mount further comprises a circumferential flange 186 with a number of distally facing projections 189 serving as a coupling means for the cartridge holder as will be described in detail below. A hub mount of the shown type is described in U.S. Pat. No. 5,693,027. The cartridge holder is adapted to receive and hold the cartridge in a loaded position, the holder having a generally tubular configuration with a distal opening adapted to axially receive the cartridge in a proximal direction, the holder and the cartridge being provided with corresponding coupling means allowing a cartridge to be mounted and subsequently released. The shown embodiment comprises a main cartridge holder portion 130 on which an axially sliding locking member 140 is arranged, the locking member comprising two opposed arms 144 each having distal gripping means 149 adapted for engagement with the cartridge flange 186. An example of an expelling mechanism allowing a user to set a desired dose as well as comprising a cartridge actuated coupling allowing the piston rod to be pushed back by a cartridge during loading is disclosed in e.g. US 2004/0210199 hereby incorporated by reference. FIG. 2 shows the cartridge 180 mounted in the cartridge holder 110.

As appears, FIG. 1 shows a drug delivery device of the front-loaded type in which a cartridge is inserted through a distal opening in the cartridge holder which in non-removable attached to the main part of the device, however, presently the most common type of non-disposable drug delivery device on the market comprises a cartridge holder adapted to be removed from the device main portion and in which a cartridge is received and removed through the proximal opening.

Although the logging unit of the present invention in one configuration is intended to be used in combination with existing types of drug delivery devices, it may be necessary to modify the design of the piston engaging part of the piston rod. More specifically, most existing piston rods of the type which rotates during expelling of a dose comprise a distal piston-engaging foot or washer allowing the piston rod to freely rotate during out-dosing. Correspondingly, a modified piston rod foot should allow a piston rod engaging structure on the logging unit to engage the piston rod non-rotationally, e.g. through a central opening in the piston rod foot. Under standard use conditions the piston rod foot should ensure non-rotational engagement with the elastomeric piston and be freely rotational relative to the piston rod. If the logging unit is supplied as part of a disposable delivery device the piston rod may comprise no foot.

Figure 3:
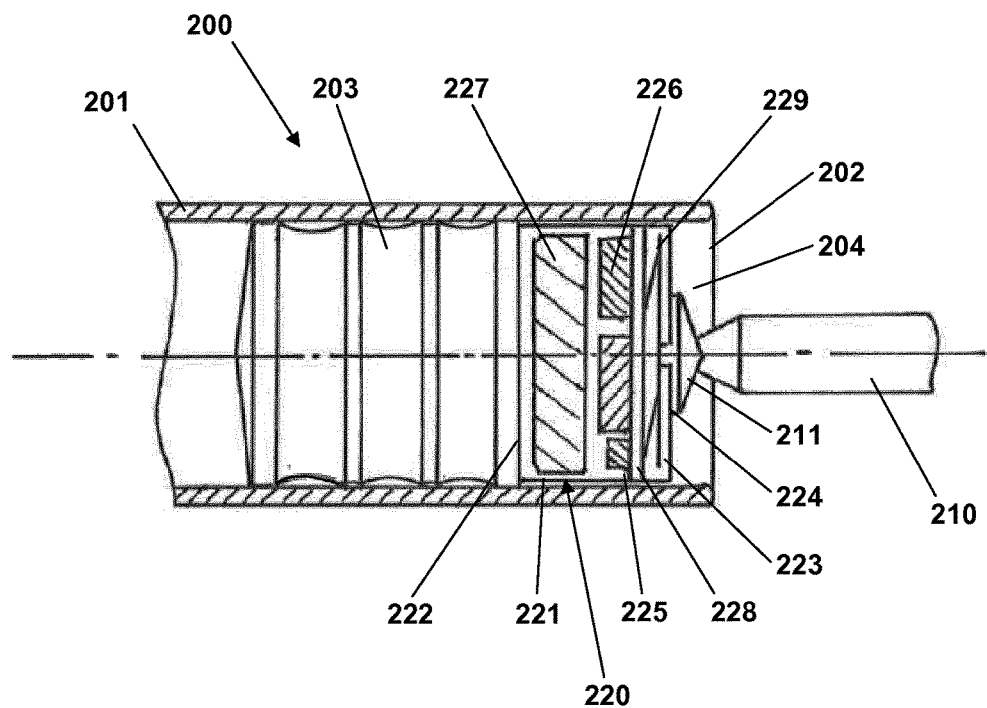
FIG. 3 shows a schematic representation of a logging unit arranged between a cartridge piston and a piston rod.

In FIG. 3 a schematic representation of a logging unit arranged between a cartridge piston and a piston rod is shown. The drug-filled cartridge 200 comprises a generally tubular main portion 201 with a proximal opening 202, a distal outlet portion (see FIG. 1), and an axially displaceable elastomeric piston 203 arranged in the tubular main portion at a distance from the proximal opening, an outer cavity 204 being formed between the piston and the proximal opening. The cartridge is arranged in a drug delivery device (not shown) comprising drug expelling means having an axially displaceable piston rod 210 with a foot 211 adapted to move the piston of the cartridge in a distal direction to thereby expel drug from the cartridge, the piston rod rotating relative to the cartridge during axial movement. An electronic logging unit 220 is arranged in the cartridge outer cavity and is configured to be moved further distally together with the piston by the piston rod. The logging unit comprises a sealed and essentially closed housing in which sensor means adapted to detect the amount of relative rotation between the piston rod and the cartridge during expelling of a dose of drug is arranged, the detected amount of relative rotation corresponding to the dose amount of drug expelled.

More specifically, the housing 221 has a generally cylindrical configuration with an outer diameter slightly smaller than the inner diameter of the cartridge in combination with which the logging unit is intended to be used. The circumferential portion of the housing may be provided with elastic means engaging the cartridge inner wall, e.g. flexible fingers (not shown), preventing the unit from rattling. If the logging unit is intended to be placed in and removed from the cartridge manually such flexible fingers should support safe and easy operation. The housing comprises a generally planar distal surface 222 adapted to non-rotationally engage the piston proximal surface, e.g. by means of friction or a number of projections, e.g. spikes. If the logging unit is not intended to be removed from the cartridge after use it may be supplied permanently attached to the piston. The opposed proximal housing surface 223 is also substantially planar and is provided with a piston rod engaging member 224 rotationally mounted to the housing. As discussed above, the piston rod engaging member is designed to engage the distal portion of a given piston rod in a non-rotational engagement.

In the interior of the logging unit housing a first stationary portion 225 is arranged, comprising electronic circuitry 226, a battery 227 and a first rotary sensor part 228. The electronic circuitry will typically comprise a micro controller, memory and, in the shown embodiment, means for wireless upload of stored data, e.g. by means of NFC. A second rotary sensor part 229 is non-rotationally mounted relative to the rotatable piston rod engaging member. In the shown embodiment the rotary sensor comprises a first stationary rotary sensor part comprising a surface with a plurality of individual electrically conducting sensor areas arranged in a pattern and connected to the electronic circuitry, and a second rotary sensor part arranged rotationally relative to the first portion, the second rotary sensor part comprising a plurality of contacts electrically connected to each other and adapted to be in contact with conducting sensor areas on the first sensor rotary part. The sensor areas and the contacts are configured to create a pattern of contact positions indicative of a rotational position between the first and second portions, the electronic circuitry being adapted to detect changes and/or positions of the rotary sensor parts relative to each other. The code pattern may have a "resolution" of e.g. 15 degrees of rotations which for a given drug formulation and delivery device combination may correspond to 1 unit (IU) of insulin. The amount of rotation can be detected using a number of designs, e.g. each increment may be counted, or a given position may be detected absolutely within sectors of e.g. 120 or 360 degrees, a counter registering the number of completed sectors.

The logging unit may be provided with a contact allowing it to be switched on when used for the first time. For example, the piston rod engaging member may be arranged to have an initial axial position and an actuated in which it is pushed distally when pressurized by the piston rod for the first time, this actuating a contact in the interior of the housing, e.g. formed integrally with the rotary sensor as shown in FIG. 5.

As a given dose of drug, especially if large, may be divided and injected with a given pause, the logging unit may be programmed to log two dose amounts expelled within a given time window, e.g. 5 minutes, as one dose. The stored data may be in the form or rotation data only, this allowing the receiving unit, e.g. a smartphone or PC, to calculate the actual drug dose amounts based on supplied information in respect of the type of drug, type of cartridge, and type of device. Alternatively, the logging unit may be pre-programmed to work only with a given drug in a given device, this especially being the case when the logging unit is supplied as part of a cartridge or as part of a pre-filled drug delivery device.

Figure 4:
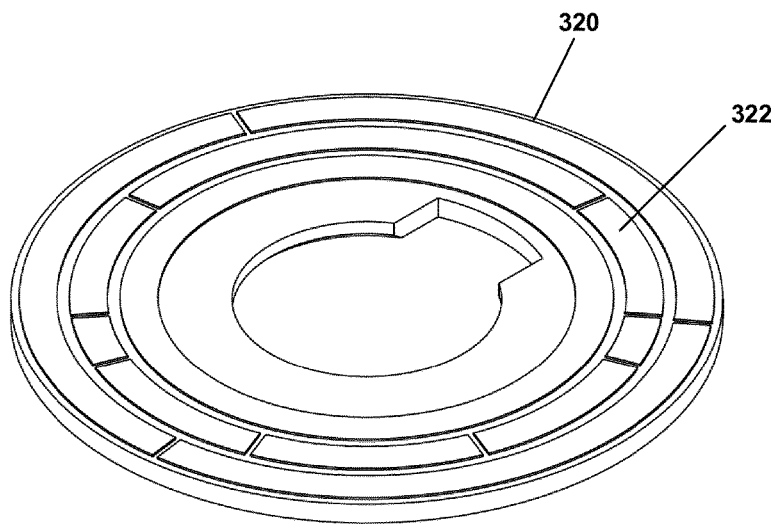
FIGS. 4 and 5 show first respectively second rotary sensor parts of the module of FIG. 3.
Figure 5:
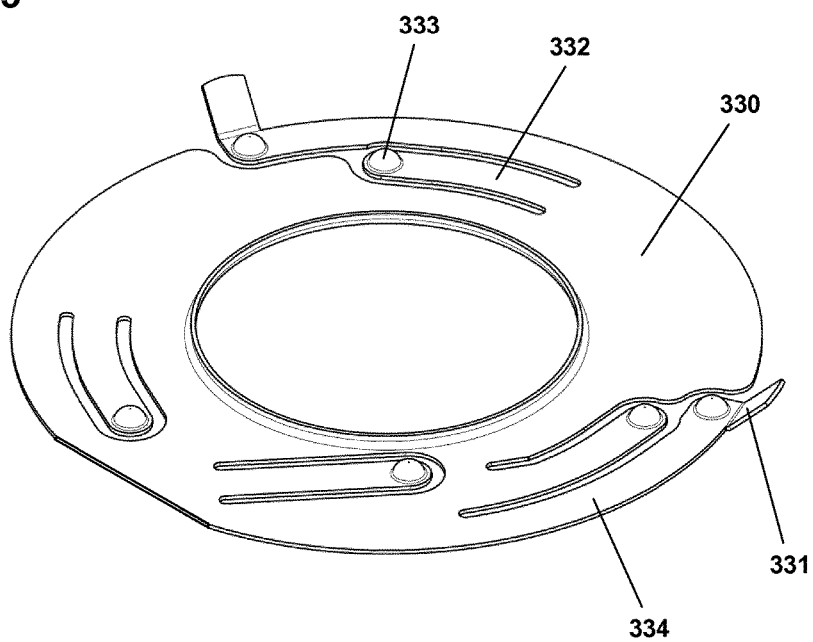

FIGS. 4 and 5 show an exemplary embodiment of a pair of rotary sensor parts of the above-described type having a stationary sensor part comprising a surface with a plurality of individual electrically conducting sensor areas arranged in a pattern, and a second rotary sensor part comprising a number of flexible contact arms electrically connected to each other and adapted to be in contact with the corresponding conducting sensor areas on the first sensor rotary part. The shown embodiment further comprises axially actuated switch arms.

More specifically, FIG. 4 shows the first rotary sensor part 320 comprising a ring-formed disc formed from circuit board material and on which a number of contact areas 322 has been plated on forming three concentric rings, an inner, an intermediate and an outer ring. In the shown embodiment the inner ring is a single contact area used as ground, whereas the intermediate and outer rings comprise a number of discrete arch-formed contact area segments, at least a portion of the segments being individually connected terminals of to the electronic circuitry mounted on the rear (distal) face of the disc. If a given segment is not connected to a terminal it can be considered a passive segment. The second rotary sensor part 330 shown in FIG. 5 is in the form of a metallic disc comprising a number of flexible arc-formed contact arms 332 protruding proximally (although the entire disc appears to be planar in the figure), the distal end of each contact arm comprising a contact point 333 adapted to create a galvanic connection with a given contact area. In this way a given pair of contact arms provides a contact structure adapted to create electric contact between two contact areas. In the shown embodiment one contact arm is provided to be in contact with the single contact area of the inner concentric ring, three contacts arms are provided to be in contact with the contact areas of the intermediate concentric ring, and two outer switch contact arms 334 are provided to be in contact with the contact areas of the outer concentric ring, the outer contact arms carrying a laterally extending projection 331. The switch contacts are used to turn on the electronics when the module is used for the first time. In the shown embodiment the inner and intermediate arms and contact areas provide the rotary sensor contacts whereas the outer arms and contact areas provide an axial switch. The two outer arms 334 are in the shown embodiment used to provide redundancy for the axial switch, however, in cooperation with the contact areas of the outer ring they could additionally be used to provide rotational information. For a given rotational position the electrically connected arms create a number of "on" galvanic contacts between given pairs of contact areas, other non-connected areas representing an "off" contact condition. The shown rotary sensor has a resolution of 15 degrees such that for each 15 degrees of rotation a pre-determined change in which of the individual rotary contacts are on and off is created. As each active contact area is connected to the electronic circuitry 226 it is possible to determine the relative rotational position between the two rotary sensor parts.

In the shown embodiment the code pattern has a step "resolution" of 15 degrees of rotations which for a given drug formulation and delivery device combination may correspond to 1 unit (IU) of insulin. Indeed, for a drug formulation having the double concentration a 7.5 degree rotary resolution would be necessary to register dose steps corresponding to 1 IU of insulin. The rotary sensor comprising the rotary contacts and the associated electronic circuitry could be designed to detect the amount of rotation using a number of designs, e.g. each 15 degrees increment may be counted, or a given position may be detected absolutely within sectors of e.g. 120 or 360 degrees, a counter registering the number of completed sectors. Such a counter could be implemented using the switch arms and outer contact areas described with reference to FIGS. 4 and 5. With a "counting" design it is important that the first increment is registered, however, modern electronics can be operated in a low-power "on" state avoiding the delay normally associated with a wake-up change of state from a "sleep" state to an "on" state.

In an exemplary embodiment the rotary sensor is designed to count the number of steps during expelling, with the expelling steps being registered in the log as the dose being expelled. As a given dose of drug, especially if large, may be divided and injected with a given pause, the logging module may be programmed to log two dose amounts expelled within a given time window, e.g. 15 minutes, as one dose.

Figure 6:
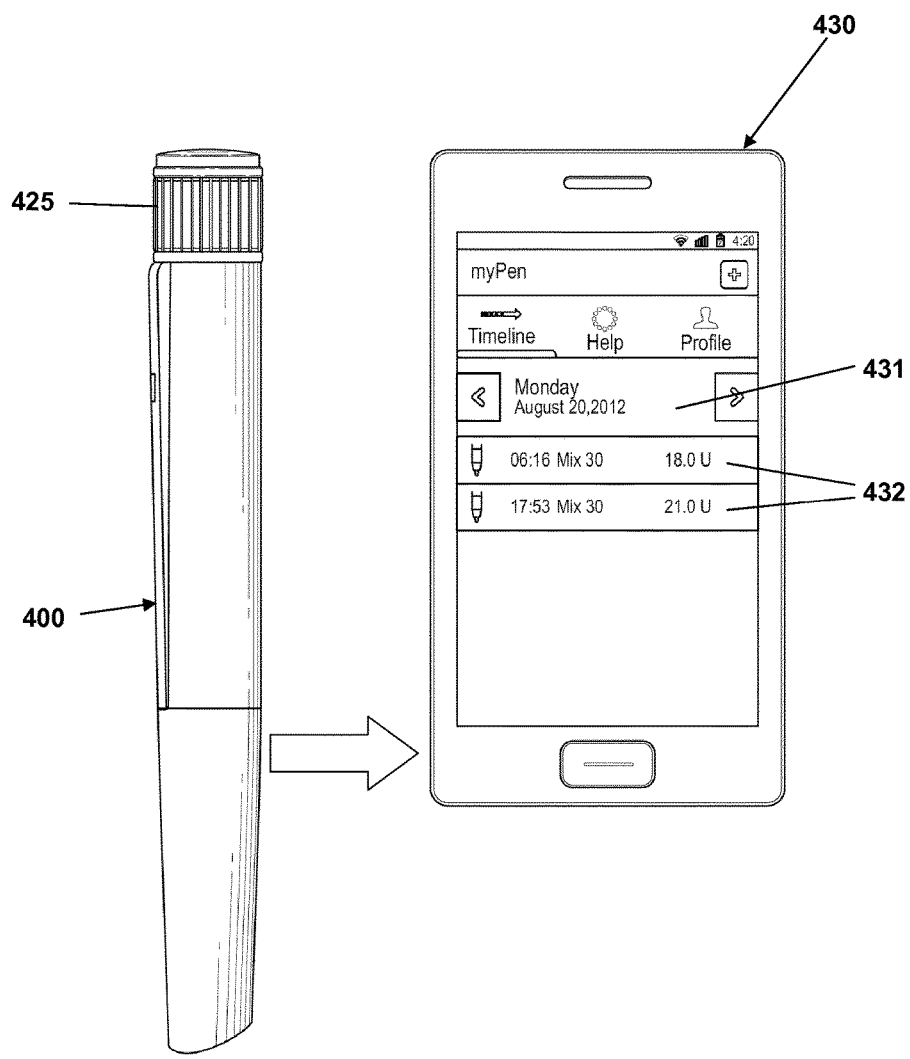
FIG. 6 shows a drug delivery pen provided with a logging module and in communication with a smartphone.

FIG. 6 shows a drug delivery pen 400 comprising a dose setting member 425 and being provided with a cartridge-mounted logging module as described above, the pen being arranged next to a smartphone 430 configured to receive logging data from the logging module via wireless communication, e.g. NFC.

In order to communicate with the logging module the smartphone has been provided with specific "insulin diary" software. When the software is activated to initiate data transfer the smartphone NFC transmitter will transmit specific code which will wake up any nearby logging module which will then retransmit a unique code identifying the specific module. The module may transmit information in respect of the drug in the cartridge, e.g. "Mix 30" as shown. In this way the smartphone can create an insulin diary indicate the specific drug.

In the shown embodiment log data from a logging module associated with a Mix 30 insulin has been transferred. In the exemplary user interface the user can toggle back and forth between different day views, each day view showing the different amounts of drug delivered together with a real time value. In FIG. 6 on a given day 431 first and second amounts 432 of Mix 30 has been delivered with the time and amount shown for each delivery.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An electronic logging unit configured to be located within an outer cavity of a cartridge configured to hold a drug, the cartridge comprising a tubular main portion with a proximal opening, a distal outlet portion, and an axially displaceable piston arranged in the tubular main portion at a distance from the proximal opening, the outer cavity being formed between the piston and the proximal opening, the electronic logging unit comprising:
a longitudinal axis,
a first distal portion adapted to engage the axially displaceable piston of the cartridge and move axially with the piston during dose expelling,
a second proximal portion adapted to engage a rotating element having a rotational axis corresponding to the longitudinal axis,
the first distal portion and the second proximal portion comprising a sensor structure, wherein the sensor structure is configured to detect relative rotation between the axially displaceable piston and the rotating element, and
storage structure adapted to store data representing detected amounts of relative rotation.

2. An electronic logging unit as in claim 1,
wherein the first distal portion of the sensor structure comprises:
electronic circuitry, and
a first rotary sensor part,
wherein the second proximal portion of the sensor structure comprises:
a second rotary sensor part.

3. An electronic logging unit as in claim 2, wherein:
(i) the first rotary sensor part comprises a pattern of a plurality of individual electrically conducting sensor areas connected to the electronic circuitry, and
(ii) the second rotary sensor part comprises at least one contact structure adapted to engage and connect different sensor areas as the first and second part of the rotary sensor rotate relative to each, the connections being indicative of a rotational position between the first and second portions.

4. An electronic logging unit as in claim 1, wherein the electronic logging unit further comprises transmitter structure adapted to transmit stored data to an external receiver.

5. An electronic logging unit as in claim 1, wherein the electronic logging unit has an effective diameter of less than 30 mm.

6. An electronic logging unit as in claim 1 in combination with the cartridge comprising a tubular main portion with a proximal opening, a distal outlet portion, and an axially displaceable piston arranged in the tubular main portion at a distance from the proximal opening, an outer cavity being formed between the piston and the proximal opening,
wherein the electronic logging unit is housed in the cartridge outer cavity.

7. An electronic logging unit as in claim 1 in combination with a drug delivery device comprising:
the drug-filled cartridge comprising:
a generally tubular main portion with a proximal opening,
a distal outlet portion, and
an axially displaceable piston arranged in the tubular main portion at a distance from the proximal opening, an outer cavity being formed between the piston and the proximal opening,
drug expelling structure comprising an axially displaceable piston rod adapted to move the piston of a cartridge in a distal direction to thereby expel drug from the cartridge, the piston rod rotating relative to the cartridge during axial movement,
wherein the electronic logging unit initially is arranged at least partly in the cartridge outer cavity and being configured to be moved fully there into, the sensor structure being adapted to detect the amount of relative rotation between the piston rod and the cartridge during expelling of a dose of drug, the amount of relative rotation corresponding to the dose amount of drug expelled, the storage structure adapted to store data representing expelled dose amounts.

8. An electronic logging unit in combination with a drug delivery device as in claim 7,
wherein engagement of the first portion and the piston prevents rotational movement there between during expelling of a dose of drug, and engagement of the second portion and the piston rod prevents rotational movement there between during expelling of a dose of drug, and
wherein the first and second portion are adapted to be moved axially corresponding to axial movement of the piston and piston rod.

9. An electronic logging unit in combination with a drug delivery device as in claim 7, wherein the piston rod during expelling of a dose exerts a force on the electronic logging unit, the force being transferred to the piston by the electronic logging unit.

10. An electronic logging unit as in claim 1,
wherein a first proximal portion of the sensor structure comprises:
electronic circuitry, and
a first rotary sensor part,
wherein the second proximal portion of the sensor structure comprises:
a second rotary sensor part.

11. An electronic logging unit as in claim 10, wherein:
(i) the first rotary sensor part comprises a pattern of a plurality of individual electrically conducting sensor areas connected to the electronic circuitry, and
(ii) the second rotary sensor part comprises at least one contact structure adapted to engage and connect different sensor areas as the first and second part of the rotary sensor rotate relative to each, the connections being indicative of a rotational position between the first and second portions.

12. An electronic logging unit in combination with the drug delivery device as in claim 9, wherein: the force is used to activate a contact to thereby turn on the electronic logging unit.

13. A method for providing a drug delivery device adapted to create a log for expelled amounts of a drug, comprising:
providing a drug-filled cartridge comprising:
a generally tubular main portion with a proximal opening,
a distal outlet portion, and
an axially displaceable piston arranged in the tubular main portion at a distance from the proximal opening, an outer cavity being formed between the axially displaceable piston and the proximal opening,
providing a drug delivery device adapted to receive the drug-filled cartridge, comprising drug expelling structure comprising:
dose setting structure allowing a user to set a dose of drug to be expelled from the received drug-filled cartridge,
an axially displaceable piston rod adapted to move the axially displaceable piston of the received drug-filled cartridge in a distal direction to thereby expel drug from the drug-filled cartridge, the axially displaceable piston rod rotating relative to the drug-filled cartridge during axial movement,
providing an electronic logging unit adapted to be arranged initially at least partly in the drug-filled cartridge outer cavity and being configured to be moved fully into the drug-filled cartridge outer cavity, the electronic logging unit comprising:
a longitudinal axis,
a first distal portion adapted to engage the axially displaceable piston of the cartridge,
a second proximal portion adapted to engage the piston rod having a rotational axis corresponding to the longitudinal axis,
the first distal portion and the second proximal portion comprising a sensor structure, wherein the sensor structure is configured to detect relative rotation between the axially displaceable piston rod and the axially displaceable piston of the drug-filled cartridge during expelling of a dose of drug, and
storage structure adapted to store data representing expelled dose amounts,
arranging the drug-filled cartridge and the electronic logging unit in the drug delivery device, the electronic logging unit being arranged at least partly in the drug-filled cartridge outer cavity.

* * * * *